US008058437B2

(12) United States Patent
Bauer et al.

(10) Patent No.: US 8,058,437 B2
(45) Date of Patent: Nov. 15, 2011

(54) (PYRROLOQUINOXALINYL) PYRAZINECARBOHYDRAZIDE-OXALIC ACID CO-CRYSTAL FOR TREATMENT OF CANCER AND OTHER DISEASES

(75) Inventors: Victor J Bauer, Bridgewater, NJ (US); Mike H O'Neill, Painesville, OH (US); Barbara J Kidon, Chardon, OH (US); Burkhard Jansen, La Jolla, CA (US)

(73) Assignee: Novelix Pharmaceuticals, Inc., La Jolla, CA (US)

( * ) Notice: Subject to any disclaimer, the term of this patent is extended or adjusted under 35 U.S.C. 154(b) by 0 days.

(21) Appl. No.: 12/937,245

(22) PCT Filed: Apr. 8, 2009

(86) PCT No.: PCT/US2009/039961
§ 371 (c)(1),
(2), (4) Date: Oct. 8, 2010

(87) PCT Pub. No.: WO2009/126743
PCT Pub. Date: Oct. 15, 2009

(65) Prior Publication Data
US 2011/0034473 A1 Feb. 10, 2011

Related U.S. Application Data

(60) Provisional application No. 61/043,380, filed on Apr. 8, 2008.

(51) Int. Cl.
*C07D 241/42* (2006.01)
*A61K 31/498* (2006.01)
(52) U.S. Cl. ........................................ 544/344; 514/250
(58) Field of Classification Search .................. 544/344; 514/250
See application file for complete search history.

(56) References Cited

U.S. PATENT DOCUMENTS
2006/0142294 A1* 6/2006 Neamati et al. ............... 514/249
2006/0235034 A1 10/2006 Neamati

OTHER PUBLICATIONS

Dermer, G.B. Bio/Technology, 1994, 12:320.*
Sausville et al. Cancer Research, 2006, vol. 66, pp. 3351-3354.*
Johnson et al. British J. of Cancer, 2001, 84(10):1424-1431.*
Grande et al. Bioorganic & Medicinal Chemistry, 2007, vol. 15, pp. 288-294.*
Stahl et al., "Handbook of Pharmaceutical Salts: Properties, Selection, and Use." (2002).
International Search Report and Written Opinion issued in International application No. PCT/US09/39961 on May 20, 2009.

* cited by examiner

*Primary Examiner* — James Anderson
(74) *Attorney, Agent, or Firm* — Knobbe, Martens Olson & Bear, LLP

(57) ABSTRACT

A novel co-crystal of N'-(7-fluoropyrrolo[1,2a]quinoxalin-4-yl)pyrazine-2-carbohydrazide with oxalic acid is disclosed. The disclosed oxalic acid co-crystal demonstrates cancer cell growth inhibition and is more bioavailable than the corresponding free base when administered as a suspension.

12 Claims, 26 Drawing Sheets

Comparison of the Sensitivity of Cancer Cell Lines to NVX-412
(GI$_{50}$ average)

| Breast Cancer | |
|---|---|
| MCF7 | 252 nM |
| NCI/ADR- | 139 nM |
| MDA-MB- | 411 nM |
| HS578T | 3.1 µM |
| T-47D | 221 nM |
| MDA-MB- | 184 nM |

| Ovarian Cancer | |
|---|---|
| NCI-ADR- | 166 nM |
| OVCAR-3 | 428 nM |
| OVCAR-4 | 142 nM |
| OVCAR-5 | 1.2 µM |
| OVCAR-8 | 258 nM |
| SK-OV-3 | 70 nM |

| CNS Cancer | |
|---|---|
| SF-268 | 250 nM |
| SF-295 | 55 nM |
| SF-539 | 256 nM |
| SNB-19 | 169 nM |
| SNB-75 | 9.9 µM |
| U251 | 99 nM |

| Leukemia | |
|---|---|
| CCRF-CEM | 31 nM |
| HL60 | 52 nM |
| K-562 | 105 nM |
| MOLT-4 | 41 nM |
| RPMI-8226 | 110 nM |
| SR | 32 nM |

| NSCLC | |
|---|---|
| A549/ATCC | 195 nM |
| EKVX | 51 nM |
| HOP-62 | 103 nM |
| HOP-92 | 313 nM |
| NCI-H226 | 82 µM |
| NCI-H23 | 530 nM |
| NCI-H322M | 17 nM |
| NCI-H460 | 44 nM |
| NCI-H522 | 235 nM |

| Colon Cancer | |
|---|---|
| COLO205 | 49 nM |
| HCC-2998 | 156 nM |
| HCT-116 | 83 nM |
| HCT-15 | 42 nM |
| HT29 | 241 nM |
| KM12 | 362 nM |
| SW-620 | 252 nM |

| Prostate Cancer | |
|---|---|
| PC-3 | 266 nM |
| DU-145 | 290 µM |

| Renal Cancer | |
|---|---|
| 786-0 | 199 nM |
| A498 | 453 nM |
| ACHN | 64 nM |
| CAKI-1 | 36 nM |
| SN12C | 183 nM |
| TK-10 | 27 nM |
| UO-31 | 62 nM |
| RXF-393 | 428 nM |

| Melanoma | |
|---|---|
| LOXIMVI | 81 nM |
| MALME-3M | 75 nM |
| M14 | 199 nM |
| SK-MEL-2 | 434 nM |
| SK-MEL-28 | 296 nM |
| SK-MEL-5 | 73 nM |
| UACC-257 | 370 nM |
| UACC-62 | 83 nM |
| MDA-MB-435 | 306 nM |

FIGURE 1

Semi-log Plot of Individual and Mean Concentration-Time Data for NVX-144 Dosed Intravenously

Semi-log Plot of Individual and Mean Concentration-Time Data for NVX-412 Dosed Orally in Solution

(PYRROLOQUINOXALINYL) PYRAZINECARBOHYDRAZIDE-OXALIC ACID CO-CRYSTAL FOR TREATMENT OF CANCER AND OTHER DISEASES

BACKGROUND

1. Field

This disclosure relates to co-crystals of nitrogen-containing heterocycles with carboxylic acids for the treatment of diseases.

2. Description of the Related Art

Neamati et al. reported nitrogen-containing heterocycles for the treatment of cancer and disorders associated with angiogenesis function (see U.S. patent application Ser. No. 11/265,593; Grande et al., "Synthesis and Antitumor Activities of a Series of Novel Quinoxalinhydrazines," *Bioorg. Med. Chem.* 15, 288-94 (2007), which are expressly incorporated herein by reference in their entireties). These nitrogen-containing heterocycles include compounds of Formula II:

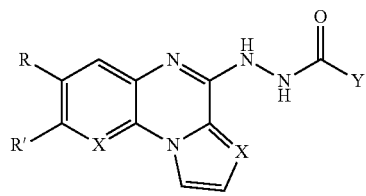

wherein R is H, alkyl, or halogen; R' is H, alkyl, or halogen; X is CH or N; and Y comprises a homocyclic or heterocyclic ring, wherein Y is 3-, 5-, or 6-pyrazinyl or 3-, 4-, 5-, or 6-pyridinyl when R is H, R' is H, X is CH, and Y is pyrazinyl or pyridinyl. One example reported therein is N'-(7-fluoropyrrolo[1,2a]quinoxalin-4-yl)pyrazine-2-carbohydrazide ("NVX-144"):

NVX-144

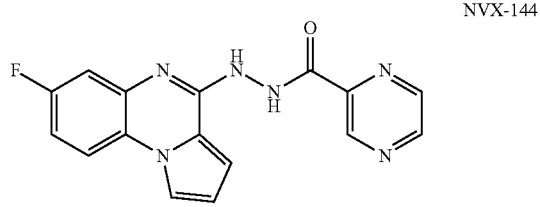

Aaker̈oy et al. discuss the advantages of co-crystals of nitrogen-containing heterocycles with carboxylic acids over the corresponding salts (see Aakeröy et al., "Cocrystal or Salt: Does It Really Matter?" *Mol. Pharmaceutics*, 4, 317-22 (2007), the entirety of which is expressly incorporated herein by reference). They report that salt formation, resulting from proton transfer from the acid to the base, is almost ten times more likely to result in a lattice with an unpredictable chemical (solvate) or stoichiometric composition than is molecular co-crystal formation, where no proton transfer occurs. They conclude that the resultant simplification of structure prediction and targeted supramolecular synthesis should allow increased diversity of accessible solid forms of drug substances that exhibit desirable properties.

SUMMARY

A novel co-crystal of N'-(7-fluoropyrrolo[1,2a]quinoxalin-4-yl)pyrazine-2-carbohydrazide with oxalic acid ("NVX-412") is disclosed. The disclosed oxalic acid co-crystal demonstrates cancer cell growth inhibition and is more bioavailable than the corresponding free base when administered as a suspension.

BRIEF DESCRIPTION OF THE DRAWINGS

FIG. 1 shows results from the treatment of a standard panel of National Cancer Institute cancer cell lines (NCI60) with NVX-412.

DETAILED DESCRIPTION OF THE PREFERRED EMBODIMENTS

Figure 2:
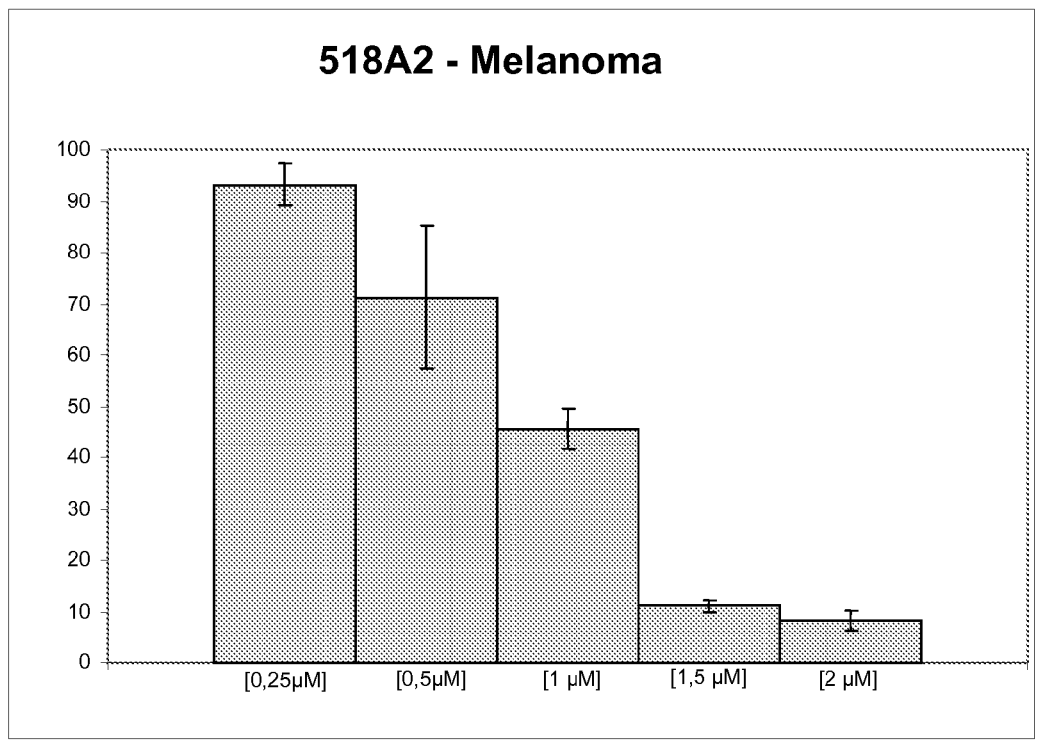
FIG. 2 shows results from the treatment of the 518A2 melanoma cell line with NVX-412.
Figure 3:
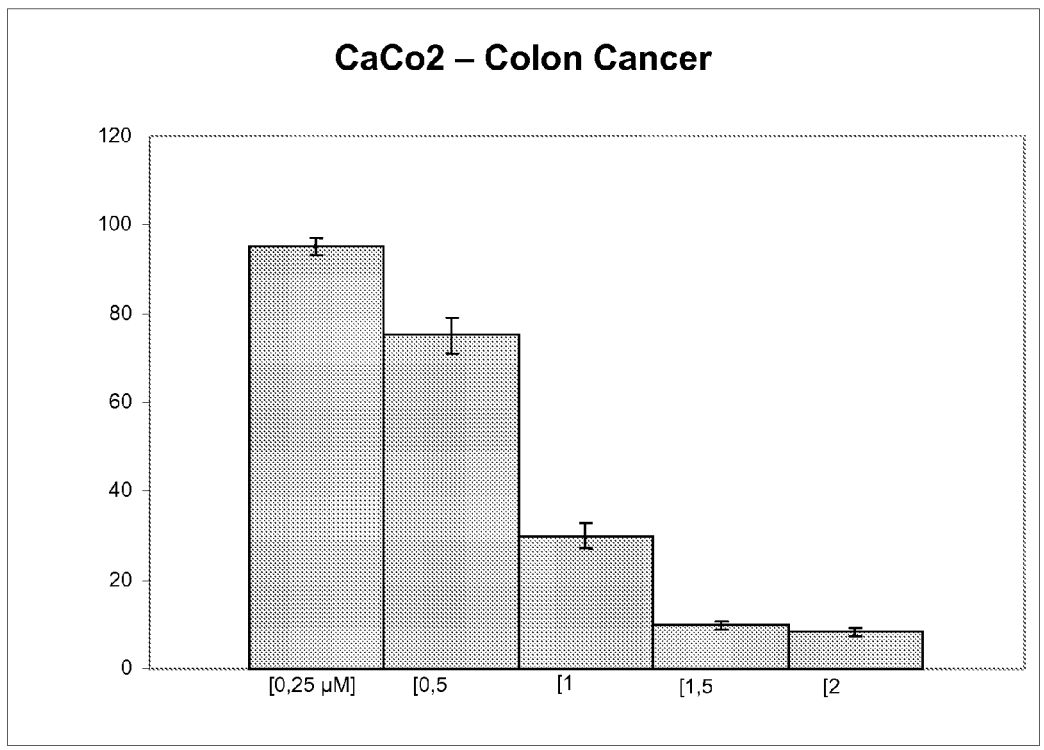
FIG. 3 shows results from the treatment of the CaCo2 colon carcinoma cell line with NVX-412.
Figure 4:
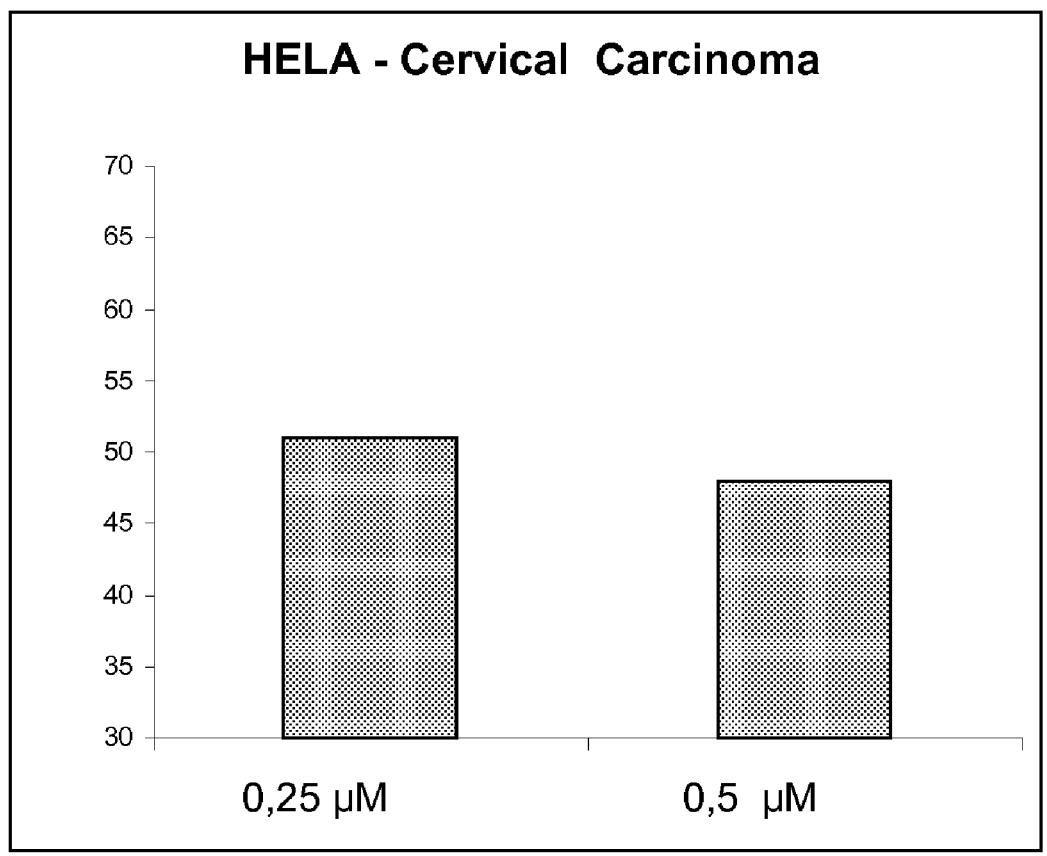
FIG. 4 shows results from the treatment of the HELA cervical carcinoma cell line with NVX-412.
Figure 5:
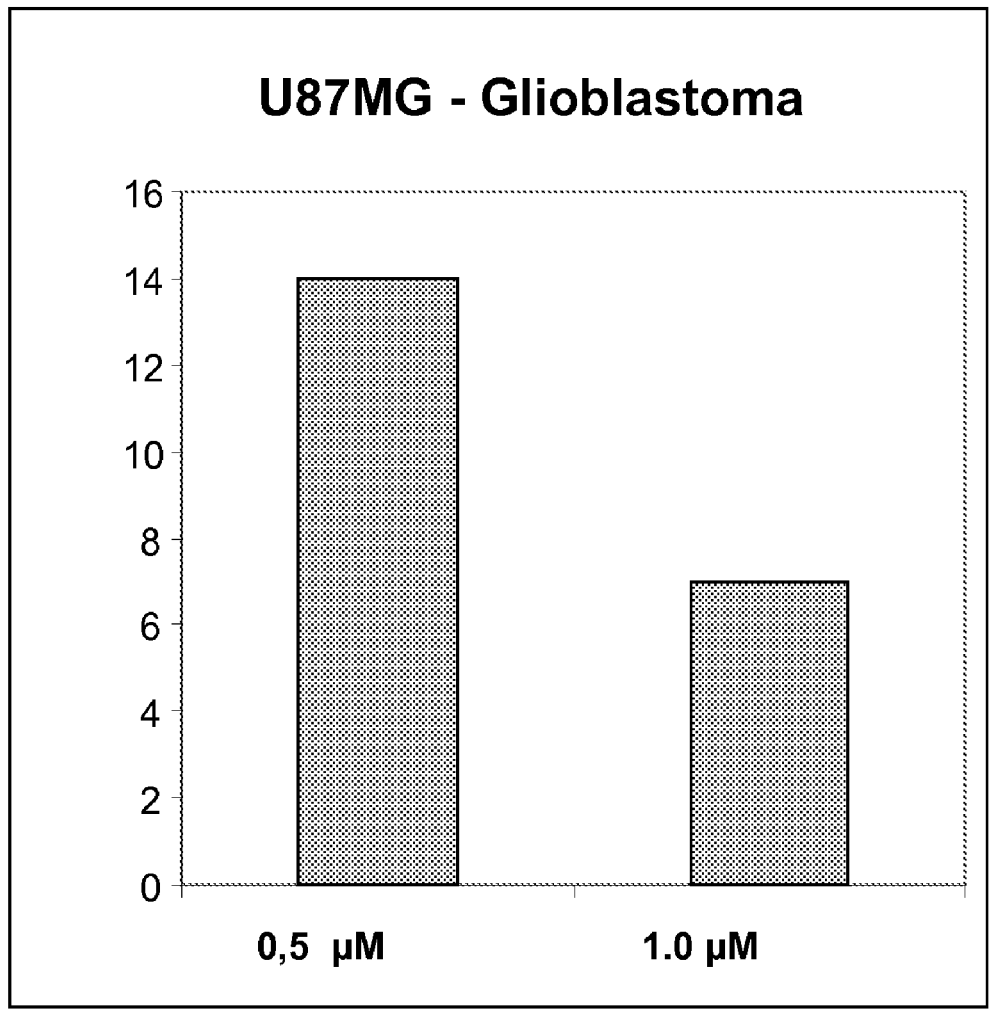
FIG. 5 shows results from the treatment of the U87MG glioblastoma cell line with NVX-412.

NVX-144.HCl exists as fluffy, statically-charged, hygroscopic crystals; these physical characteristics can be problematic in formulation of oral dosage forms like tablets and capsules. Thus, a series of experiments was conducted to assess the preparation of NVX-144 salts of acids other than hydrochloric acid as possible novel compounds better suited to pharmaceutical preparations. These experiments demonstrated that the free NVX-144 base (prepared from NVX-144.HCl) was a very weak base, and thus did not form salts with typical weak organic acids. As expected, NVX-144 base readily formed salts with strong organic acids. However, most unexpectedly, treatment of NVX-144 base with oxalic acid resulted in formation of a novel crystalline substance with properties inconsistent with that of the expected NVX-144 oxalate salt. Evaluation of spectral properties of the novel NVX-144-oxalic acid product indicated that a new NVX-144-oxalic acid co-crystal ("NVX-412") was formed, having the following structure:

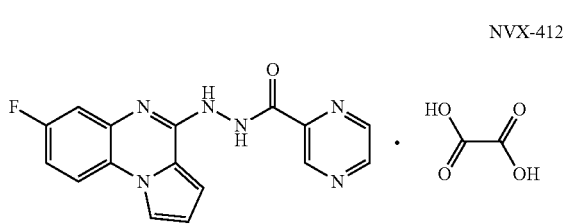

NVX-412

Although oxalic acid co-crystals are rare, Trask et al. have reported a co-crystal of caffeine with oxalic acid (see Trask et al., "Pharmaceutical Cocrystallization: Engineering a Remedy for Caffeine Hydration," *Crystal Growth & Design*, 5, 1013-21 (2005)). It was discovered that NVX-412 forms stable mono- and di-hydrates suitable for pharmaceutical formulation and is useful in the treatment of various diseases.

Synthesis of NVX-412

As described in detail below, the oxalic acid co-crystal NVX-412 was generated from the NVX-144 free base. NVX-144.HCl was first synthesized by adding pyrazinoic acid hydrazide to a 4-chloro-7-fluoropyrrolo[1,2a]quinoxaline solution. The isolated hydrochloride salt NVX-144.HCl was then neutralized with aqueous sodium hydroxide to generate NVX-144 free base. The isolated free base NVX-144 was then added to an oxalic acid solution to generate NVX-412.

EXAMPLE 1

Preparation of N'-(7-fluoropyrrolo[1,2a]quinoxalin-4-yl)pyrazine-2-carbohydrazide hydrochloride (NVX-144.HCl). To a solution of 8.0 g of 4-chloro-7-fluoropyrrolo[1,2a]quinoxaline in 100 mL ethanol was added 5.0 g pyrazinoic acid hydrazide with stirring under argon. The mixture was stirred for 4 hours and filtered to provide 11 g (94%) of NVX-144.HCl as off-white crystals, mp 282° C., purity by LC/MS 98%. $^1$H-NMR (300 MHz, DMSO-$d_6$) δ: 7.03 (m, 1H), 7.41 (t, 1H), 7.73 (m, 2H), 8.37 (dd, 1H), 8.65 (bs, 1H), 8.90 (m, 1H), 9.01 (d, 1H), 9.30 (s, 1H), 11.69 (bs, 1H). Analysis: Calcd. for $C_{16}H_{12}N_6ClFO$: C, 53.57; H, 3.37; N, 23.43; Cl, 9.88; F, 5.30. Found: C, 53.70; H, 3.41; N, 23.29; Cl, 9.92; F, 5.21. HRMS Calcd. 322.0978. Found 322.0984. UV $\lambda_{max}$ 220 nm. FTIR (neat) 3084, 1673, 1929 $cm^{-1}$.

EXAMPLE 2

Preparation of N'-(7-fluoropyrrolo[1,2a]quinoxalin-4-yl)pyrazine-2-carbohydrazide (NVX-144). A mixture of 4.5 g NVX-144.HCl, 100 mL water, and 100 mL acetonitrile was heated to form a solution. The solution was adjusted to pH 7 with 6.5 mL 2N sodium hydroxide with stirring and was allowed to cool to room temperature, upon which a precipitate separated. The mixture was filtered to provide 3.0 g (68%) of NVX-144 as off-white crystals, mp 166-170° C., purity by LC/MS 96%. $^1$H-NMR (300 MHz, DMSO-$d_6$) δ: 6.81 (m, 1H), 7.13 (m, 1H), 7.20 (m, 2H), 8.15 (dd, 1H), 8.33 (m, 1H), 8.85 (m, 1H), 8.96 (m, 1H), 9.24 (m, 1H), 9.78 (bs, 1H), 10.96 (bs, 1H). LC/MS m/z 323.1 [M+H]$^+$. UV $\lambda_{max}$ 225 nm. FTIR (neat) 3117, 1671, 1489 $cm^{-1}$.

EXAMPLE 3

Preparation of N'-(7-fluoropyrrolo[1,2a]quinoxalin-4-yl)pyrazine-2-carbohydrazide oxalic acid co-crystal (NVX-412). To a mixture of 5.1 g NVX-144 and 590 mL water was added dropwise a solution of 3.91 g oxalic acid in 60 mL water with stirring under nitrogen. After stirring for 2 hours, the slurry was filtered, washed with water, and dried to provide 11.8 g (92%) of NVX-412 as pale yellow crystals, purity by LC/MS 99%. $^1$H-NMR (300 MHz, DMSO-$d_6$) δ: 6.8 (1H), 7.1-7.2 (3H), 8.15 (1H), 8.3 (1H), 8.85 (1H), 8.95 (1H), 9.25 (1H), 10.95 (1H).

NVX-144 readily forms salts with strong acids (e.g., hydrochloric acid, benzenesulfonic acid, p-toluenesulfonic acid), but does not form salts with weak monocarboxylic acids (e.g., acetic acid, aspartic acid, gluconic acid, lactic acid) or with stronger dicarboxylic acids (e.g., fumaric acid, malic acid, maleic acid, muconic acid, succinic acid). Thus NVX-144 would not be expected to form a salt with oxalic acid, a relatively strong dicarboxylic acid.

However, NVX-144 does form a novel entity (NVX-412) with oxalic acid that has 1:1 stoichiometry. The X-ray diffraction (XRD) pattern of NVX-412 is markedly different from that of NVX-144, demonstrating that a new crystalline substance was formed. Further, the $^1$H NMR chemical shifts for NVX-412 are different from those of NVX-144.HCl, and are essentially identical with the $^1$H NMR chemical shifts for NVX-144 base. This is the expected result for a co-crystal, as the two components are separately solvated in the NMR solution. Table 1 shows a comparison of $^1$H NMR chemical shifts for NVX-144, NVX-144.HCl, and NVX-412 in DMSO-$d_6$.

TABLE 1

Comparison of $^1$H NMR Chemical Shifts of NVX-144, NVX-144'HCl, and NVX-412 in DMSO-$d_6$.

| NVX-144 | NVX-412 | NVX-144'HCl |
|---|---|---|
| 10.96 (1H) | 10.95 (1H) | 11.69 (1H) |
| 9.78 (1H) | — | — |
| 9.24 (1H) | 9.25 (1H) | 9.30 (1H) |
| 8.96 (1H) | 8.95 (1H) | 9.01 (1H) |
| 8.85 (1H) | 8.85 (1H) | 8.90 (1H) |
| 8.33 (1H) | 8.3 (1H) | 8.65 (1H) |
| 8.15 (1H) | 8.15 (1H) | 8.37 (1H) |
| 7.20 (2H) | 7.2 (2H) | 7.73 (2H) |
| 7.13 (1H) | 7.1 (1H) | 7.41 (1H) |
| 6.81 (1H) | 6.8 (1H) | 7.03 (1H) |

Therapeutic Use of NVX-412

NVX-412 was demonstrated to be useful in the treatment of various diseases. In one embodiment, NVX-412 inhibits the growth of cancer cells. FIGS. 1-6 show the results for treatment of the following human cancer cell lines with NVX-412: CCRF-CEM (leukemia), HL-60 (leukemia), K562 (leukemia), MOLT-4 (leukemia), RPMI-8226 (leukemia), SR (leukemia), A-549 (lung cancer), EKVX (lung cancer), HOP-62 (lung cancer), HOP-92 (lung cancer), NCI-H226 (lung cancer), NCI-H23 (lung cancer), NCI-H322M (lung cancer), NCI-H460 (lung cancer), NCI-H522 (lung cancer), COLO 205 (colon cancer), HCC-2998 (colon cancer), HCT-116 (colon cancer), HCT-15 (colon cancer), HT29 (colon cancer), KM12 (colon cancer), SW-620 (colon cancer), CaCo2 (colon cancer), SF-268 (CNS cancer), SF-295 (CNS cancer), SF-539 (CNS cancer), SNB-19 (CNS cancer), SNB-75 (CNS cancer), U251 (CNS cancer), U87MG (glioblastoma), LOX IMVI (melanoma), MALME-3M (melanoma), M14 (melanoma), MDA-MB-435 (melanoma), SK-MEL-2 (melanoma), SK-MEL-28 (melanoma), SK-MEL-5 (melanoma), UACC-257 (melanoma), UACC-62 (melanoma), 518A2 (melanoma), OVCAR-3 (ovarian cancer), OVCAR-4 (ovarian cancer), OVCAR-5 (ovarian cancer), OVCAR-8 (ovarian cancer), NCI/ADR-RES (ovarian cancer), SK—OV-3 (ovarian cancer), HELA (cervical cancer), 786-0 (renal cancer), A498 (renal cancer), ACHN (renal cancer), CAKI-1 (renal cancer), RXF 393 (renal cancer), SN12C (renal cancer), TK-10 (renal cancer), UO-31 (renal cancer), PC-3 (prostate cancer), DU-145 (prostate cancer), MCF7 (breast cancer), MDA-MB-231 (breast cancer), HS 578T (breast cancer), T-47D (breast cancer), MDA-MB-468 (breast cancer), TC71luc (Ewing's sarcoma), and TC32luc (Ewing's sarcoma). Experimental details are provided in Examples 4 and 5 below.

EXAMPLE 4

Treatment of various cancer cell lines with NVX-412. Over 60 human cancer cell lines were treated with NVX-412 according to procedures detailed by the National Cancer Institute Developmental Therapeutics Program (see dtp.nci.nih.gov/branches/btb/ivclsp.html) and Shoemaker R H (*Nat. Rev. Cancer,* 6, 813-823, (2006)) and references cited therein. Many of the cell lines tested are available from the American Type Culture Collection (Rockville, Md., USA). The melanoma cell line 518A2 has been described previously (Jansen et al., "Activated N-Ras Contributes to the Chemoresistance of Human Melanoma in Severe Combined Immunodeficiency (SCID) Mice by Blocking Apoptosis," *Cancer Research* 57, 362-65 (1997)). A typical screening of cancer cell treatment by NVX-412 employed the following procedure.

The human tumor cell lines of the cancer screening panel were grown in RPMI 1640 medium containing 5% fetal bovine serum and 2 mM L-glutamine. For a typical screening experiment, cells were inoculated into 96 well microtiter plates in 100 μL at plating densities ranging from 5,000 to 40,000 cells/well depending on the doubling time of individual cell lines. After cell inoculation, the microtiter plates were incubated at 37° C. in 5% $CO_2$/95% air at 100% relative humidity for 24 hours prior to the addition of NVX-412.

After 24 hours, two plates of each cell line were fixed in situ with TCA, to represent a measurement of the cell population for each cell line at the time of NVX-412 addition ($T_z$). NVX-412 was solubilized in dimethyl sulfoxide at 400-fold the desired final maximum test concentration and stored frozen prior to use. At the time of NVX-412 addition, an aliquot of frozen concentrate was thawed and diluted to twice the desired final maximum test concentration with complete medium containing 50 μg/mL gentamicin. Additional four, 10-fold or ½ log serial dilutions were made to provide a total of five concentrations of NVX-412 plus control. Aliquots of 100 μl of these different NVX-412 dilutions were added to the appropriate microtiter wells already containing 100 μL, of medium, resulting in the required final NVX-412 concentrations.

Following the addition of NVX-412, the plates were incubated for an additional 48 hours at 37° C. in 5% $CO_2$/95% air at 100% relative humidity. For adherent cells, the assay was terminated by the addition of cold TCA. Cells were fixed in situ by the gentle addition of 50 μL of cold 50% (w/v) TCA (final concentration, 10% TCA) and incubated for 60 minutes at 4° C. The supernatant was discarded, and the plates were washed five times with tap water and air dried. Sulforhodamine B (SRB) solution (100 μL) at 0.4% (w/v) in 1% acetic acid was added to each well, and plates were incubated for 10 minutes at room temperature. After staining, unbound dye was removed by washing five times with 1% acetic acid and the plates were air dried. Bound stain was subsequently solubilized with 10 mM trizma base, and the absorbance was read on an automated plate reader at a wavelength of 515 nm. For suspension cells, the methodology was the same except that the assay was terminated by fixing settled cells at the bottom of the wells by gently adding 50 μL of 80% TCA (final concentration, 16% TCA). Using the seven absorbance measurements [time zero ($T_z$), control growth (C), and test growth in the presence of NVX-412 at the five concentration levels ($T_i$)], the percentage growth was calculated at each of the NVX-412 concentration levels. Percentage growth inhibition was calculated as:

$[(T_i-T_z)/(C-T_z)]*100$ for concentrations for which $Ti \geq Tz$ $[(T_i-T_z)/T_z]*100$ for concentrations for which $Ti<Tz$.

Three dose response parameters were calculated. Growth inhibition of 50% ($GI_{50}$) was calculated from $[(T_i-T_z)/(C-T_z)]*100=50$, which is the concentration resulting in a 50% reduction in the net protein increase (as measured by SRB staining) in control cells during the incubation. The concentration resulting in total growth inhibition (TGI) was calculated from $T_i=T_z$. The $LC_{50}$ (concentration resulting in a 50% reduction in the measured protein at the end of the treatment as compared to that at the beginning) indicating a net loss of cells following treatment was calculated from $[(T_i-T_z)/T_z]*100=-50$. Values were calculated for each of these three parameters if the level of activity was reached; however, if the effect was not reached or was exceeded, the value for that parameter was expressed as greater or less than the maximum or minimum concentration tested.

FIG. 1 shows NVX-412 concentrations required to reduce the growth of the respective cancer cell lines tested by 50% ($GI_{50}$).

In additional experiments, the results of which are shown in FIGS. 2-5, 518A2 melanoma cells, CaCo2 colon cancer cells, HELA cervical carcinoma cells, and U87MG glioblastoma cells were treated with NVX-412. The cells were maintained in Dulbecco's Modified Eagle Medium (DMEM) with 4500 mg/L glucose supplemented with 10% fetal calf serum (FCS) from Gibco BRL (Life Technologies, Berlin, Germany). For cell survival assays, cells were seeded in 24 well plates (5T/well) and treated or not treated for three days. Cell numbers were then counted and described as a percentage of untreated controls. Each data point represents the average cell number obtained from four wells. Each experiment was performed three times. For assessment of cell growth, the number of surviving cells at the end of the treatment period was determined using an automated cell counter from Beckman Coulter GmbH (Krefeld, Germany).

FIGS. 2-5 show the percent inhibition of tumor cell growth relative to controls after NVX-412 treatment of the indicated cancer cell lines (the mean and standard deviation (n=3) for treatment of cancer cells for three days at the indicated concentrations are depicted where applicable).

In summary, NVX-412 treatment led to pronounced inhibition of tumor cell growth; $GI_{50}$ values for almost all cell lines tested were in the nanomolar range.

EXAMPLE 5

Figure 6:
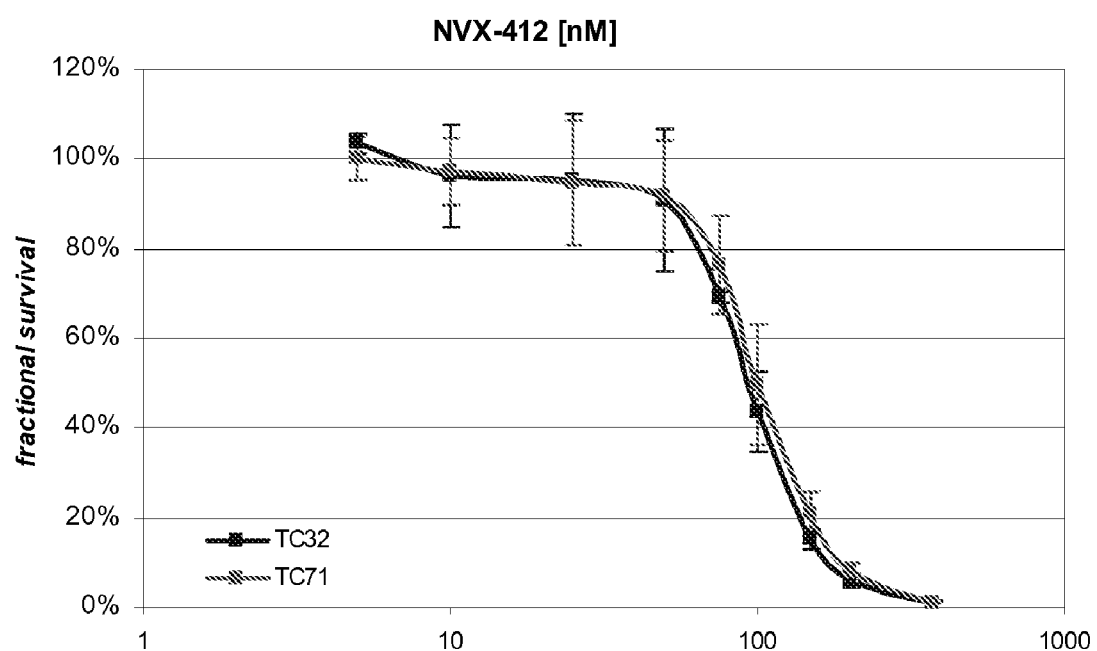
FIG. 6 shows results from the treatment of the TC32 and TC71 Ewing's sarcoma cell lines with NVX-412.

Treatment of Ewing's sarcoma with NVX-412. The TC71luc and TC32luc Ewing tumor cell lines stably express the luciferase gene. Cells were seeded into 96-well plates 24 hours before treating with the active compound to allow attachment. Cells were treated with NVX-412 for 72 hours. Serial dilutions of NVX-412 were prepared in medium from a 10 μM stock solution in DMSO. The maximum DMSO concentration in the assay was 0.1%, which did not affect cell viability (data not shown). After 72 hours, cell viability was measured by luminescence using a Saphire2 plate reader. Experiments were performed in triplicate; FIG. 6 shows the mean and standard deviation for at least three independent experiments. Table 2 shows the fraction of cells remaining after three days as a function of the concentration of NVX-412.

TABLE 2

| NVX-412 | TC71 | | TC32 | |
|---|---|---|---|---|
| (nM) | Mean | Stdev | mean | stdev |
| 5 | 1.00 | 0.050 | 1.03 | 0.024 |
| 10 | 0.97 | 0.074 | 0.96 | 0.112 |
| 25 | 0.95 | 0.140 | 0.95 | 0.147 |
| 50 | 0.92 | 0.124 | 0.91 | 0.159 |
| 75 | 0.76 | 0.107 | 0.69 | 0.013 |
| 100 | 0.50 | 0.134 | 0.44 | 0.089 |
| 150 | 0.21 | 0.052 | 0.15 | 0.022 |
| 200 | 0.08 | 0.021 | 0.06 | 0.013 |
| 375 | 0.01 | 0.003 | 0.01 | 0.003 |

In summary, NVX-412 was not only capable of inhibiting the growth of several epithelial cell lines as described above, but was also very effective against sarcoma, melanoma, and CNS cancer cell lines.

Pharmacokinetics

Pharmacokinetic experiments demonstrated increased bioavailability of NVX-412 as compared to NVX-144 when dosed as a suspension. Experimental details and results are provided in Example 6 below. The pharmacokinetic experiments demonstrated that NVX-412, when administered intravenously to rats, had a terminal plasma half-life of 0.93 to 1.15 hours, and resulted in a moderate clearance of 3806 mL/h/kg and a moderate volume of distribution of 3985 mL/kg. The oral absorption of NVX-144 and NVX-412 when administered as a solution or suspension were both moderate.

The oral bioavailability of NVX-144 averaged 34.7% after oral administration as a suspension and 46.1% after oral administration as a solution. The oral bioavailability of NVX-412 averaged 43.9% after oral administration as a suspension and 43.5% after oral administration as a solution. Thus, there was no significant difference in oral absorption between NVX-412 and NVX-144 when dosed as a solution, but there was a slight improvement in oral absorption with NVX-412 over NVX-144 free base when dosed as a suspension.

EXAMPLE 6

Pharmacokinetic Experiments for NVX-412 and NVX-144.

Dose Preparation

The oral suspension formulation was prepared by suspending the test article in 5% PEG-200/95% of a 0.5% solution of methylcellulose. The concentration of the test article was such that a dosing volume of 10 mL/kg delivered the intended dose level. The oral solution formulations of NVX-144 and NVX-412 were prepared by dissolving the test article in 10% by volume dimethyl acetamide, followed by 60% by volume PEG-400, and then adding slowly a solution of 30% Captisol® in 50 mM lactic acid to provide the remaining 30% of volume. The concentration of the test article was such that a dosing volume of 10 mL/kg delivered the intended dose level. The IV formulation of NVX-412 was prepared by dissolving the test article in 10% by volume dimethyl acetamide, followed by 10% by volume PEG-400, and then adding slowly a solution of 10% Captisol® in 50 mM lactic acid to provide the remaining 80% of volume. The concentration of the test articles was such that a dosing volume of 2.5 mL/kg delivered the intended dose level. The doses administered were based on the body weight of each animal taken shortly before dosing. The formulations were used immediately after preparation.

Study Design

A total of 15 rats were assigned to the study. Five groups of three male rats each comprised the study. Each group was treated once by oral gavage or intravenous injection via the tail vein as specified in Table 3 below.

TABLE 3

| Group Assignment, Dose Routes, and Dose Levels | | | | | | |
|---|---|---|---|---|---|---|
| Group No. | No. of Animals (M) | Test Article | Dose Route | Dose Level (mg/kg) | Dose Volume (mL/kg) | Dose Conc. (mg/mL) |
| 1 | 3 | NVX-412 | IV | 5 | 2.5 | 2.0 |
| 2 | 3 | NVX-144-FB | Oral-Suspension | 20 | 10 | 2.0 |
| 3 | 3 | NVX-412 | Oral-Suspension | 20 | 10 | 2.0 |
| 4 | 3 | NVX-144-FB | Oral-Solution | 20 | 10 | 2.0 |
| 5 | 3 | NVX-412 | Oral-Solution | 20 | 10 | 2.0 |

Test Article Administration

The animals were fasted overnight prior to dosing and the feed returned approximately 2 hours post-dosing. The dose for each animal was based on the most recent body weight. Oral doses were administered by gavage. Animals received 10 mL/kg per single oral dose. Intravenous doses were administered by tail vein injection. The dose for each animal was based on the most recent body weight. Animals were dosed at 2.5 mL/kg per single intravenous dose.

Viability Observations

Animals were observed for viability at least once in the morning and once in the evening throughout the study.

Body Weight

For all animals, body weight was measured immediately prior to dosing.

Pharmacokinetic Samples

Blood was collected from the animals in Groups 1 through 5 for pharmacokinetic analysis. Approximately 0.3 mL of blood was collected in potassium EDTA tubes via the orbital plexus at four time points (30 minutes, 1 hour, 4 hours, and 8 hours post-dose) from each rat treated by the oral route, and the blood samples were processed to prepare plasma. Blood was collected at four time points (5 minutes, 30 minutes, 1 hour, and 2 hours post-dose) from each rat treated by the intravenous route, and the blood samples were processed to prepare plasma. Animals were terminated (without necropsy) following their final sample collection.

The whole blood samples were centrifuged (~1500×g) for a minimum of 10 minutes in a refrigerated centrifuge (set at ~5° C.). Plasma was prepared and transferred within 30 minutes of blood collection/centrifugation to appropriately labeled tubes. The tubes were then frozen and stored in the dark at ≦-70° C. until analysis. The plasma samples were analyzed by LC-MS/MS to determine the plasma concentrations of NVX-144 and NVX-412. Pharmacokinetic analysis of the plasma concentration data was conducted using non-compartmental analysis with WinNonlin Version 4.1.

After intravenous administration of NVX-412 at 5 mg/kg, peak plasma concentrations were reached at 0.083 hours post-dose with an average concentration of 1842 ng/mL. Terminal plasma half-life was 1.0 hour, while the average AUC (0-∞) was 1314 h*ng/mL. After oral administration of NVX-144 free base as a suspension at 20 mg/kg, peak plasma concentrations were reached at between 0.5 and 1 hour post-dose with an average concentration of 487 ng/mL. Terminal plasma half-life was estimated at 1.4 hours, while the average AUC (0-∞) was 1826 h*ng/mL. Table 4 shows the plasma concentration data (in ng/mL) for individual animals after intravenous dosing with NVX-412.

TABLE 4

| Animal Number | Time (h) | | | |
| --- | --- | --- | --- | --- |
| | 0.083 | 0.5 | 1 | 2 |
| 202900 | 1808.86 | 488.34 | 288.08 | 167.34 |
| 202901 | 1716.72 | 481.82 | 278.84 | 185.19 |
| 202902 | 2001.77 | 461.19 | 253.02 | 143.93 |
| Mean | 1842.45 | 477.11 | 273.31 | 165.49 |
| SD | 145.46 | 14.17 | 18.17 | 20.69 |
| % CV | 7.9% | 3.0% | 6.6% | 12.5% |

Table 5 shows the calculated pharmacokinetic parameters for NVX-412 after intravenous dosing.

TABLE 5

| Animal Number | Rsq | T½ (h) | Tmax (h) | Cmax (ng/mL) | AUCall (h * ng/mL) | AUCINF (h * ng/mL) | AUC % Extrap (%) | Cl (mL/h/kg) | Vss (mL/kg) |
| --- | --- | --- | --- | --- | --- | --- | --- | --- | --- |
| 202900 | 0.9673 | 1.01 | 0.08 | 1808.9 | 1073.27 | 1315.94 | 18.44 | 3799.57 | 3956.04 |
| 202901 | 0.9273 | 1.15 | 0.08 | 1716.7 | 1043.56 | 1349.72 | 22.68 | 3704.48 | 4552.97 |
| 202902 | 0.9573 | 0.93 | 0.08 | 2001.8 | 1084.89 | 1277.84 | 15.1 | 3912.87 | 3446.35 |
| N | 3 | 3 | 3 | 3 | 3 | 3 | 3 | 3 | 3 |
| Mean | 0.9506 | 1.03 | 0.08 | 1842.5 | 1067.24 | 1314.5 | 18.74 | 3805.64 | 3985.12 |
| SD | 0.0208 | 0.11 | 0 | 145.46 | 21.32 | 35.96 | 3.8 | 104.33 | 553.88 |
| % CV | 2.2 | 10.7 | 0 | 7.9 | 2 | 2.7 | 20.3 | 2.7 | 13.9 |

After oral administration of NVX-412 as a suspension at 20 mg/kg, peak plasma concentrations were reached at 1 hour post-dose with an average concentration of 525 ng/mL. Terminal plasma half-life was estimated at 1.2 hours, while the average AUC (0-∞) was 2307 h*ng/mL. After oral administration of NVX-144 free base as a solution at 20 mg/kg, peak plasma concentrations were reached between 0.5 and 1 hour post-dose with an average concentration of 714 ng/mL. Terminal plasma half-life was estimated at 1.6 hours, while the average AUC (0-∞) was 2521 h*ng/mL.

After oral administration of NVX-412 as a solution at 20 mg/kg, peak plasma concentrations were reached between 0.5 and 1 hour post-dose with an average concentration of 643 ng/mL. Terminal plasma half-life was estimated at 1.4 hours, while the average AUC (0-∞) was 2289 h*ng/mL. The bioavailability averaged 34.7% after oral administration of NVX-144 free base as a suspension and 46.1% after oral administration as a solution. The bioavailability averaged 43.9% after oral administration of NVX-412 as a suspension and 43.5% after oral administration as a solution.

Table 6 shows the plasma concentration data (in ng/mL) for individual animals after oral dosing with NVX-144 and NVX-412.

TABLE 6

| Group | Compound dosed | Route | Animal Number | Time (hr) | | | |
| --- | --- | --- | --- | --- | --- | --- | --- |
| | | | | 0.5 | 1 | 4 | 8 |
| 2 | NVX-144 Free Base | PO-Suspension | 202903 | 436.03 | 282.56 | 270.38 | 14.92 |
| | | | 202904 | 428.07 | 401.49 | 234.64 | 12.33 |

TABLE 6-continued

| Group | Compound dosed | Route | Animal Number | Time (hr) 0.5 | 1 | 4 | 8 |
|---|---|---|---|---|---|---|---|
| | | | 202905 | 571.69 | 597.75 | 175.82 | 5.37 |
| | | | Mean | 478.60 | 427.27 | 226.95 | 10.87 |
| | | | SD | 80.72 | 159.17 | 47.75 | 4.94 |
| | | | % CV | 16.9% | 37.3% | 21.0% | 45.4% |
| 3 | NVX-412 | PO-Suspension | 202906 | 499.38 | 525.49 | 340.92 | 13.07 |
| | | | 202907 | 386.99 | 464.23 | 181.80 | BLQ |
| | | | 202908 | 573.34 | 584.12 | 249.34 | 5.48 |
| | | | Mean | 486.57 | 524.61 | 257.35 | 9.27 |
| | | | SD | 93.83 | 59.95 | 79.86 | NC |
| | | | % CV | 19.3% | 11.4% | 31.0% | NC |
| 4 | NVX-144 Free Base | PO-Solution | 202909 | 690.74 | 569.62 | 288.75 | 75.29 |
| | | | 202910 | 610.62 | 626.73 | 163.62 | 5.57 |
| | | | 202911 | 824.32 | 731.54 | 221.82 | 13.76 |
| | | | Mean | 708.56 | 642.63 | 224.73 | 31.54 |
| | | | SD | 107.96 | 82.12 | 62.62 | 38.11 |
| | | | % CV | 15.2% | 12.8% | 27.9% | 120.8% |
| 5 | NVX-412 | PO-Solution | 202912 | 731.88 | 628.26 | 259.40 | 8.53 |
| | | | 202913 | 635.82 | 686.88 | 171.97 | 5.14 |
| | | | 202914 | 509.37 | 489.07 | 298.24 | 34.89 |
| | | | Mean | 625.69 | 601.41 | 243.20 | 16.19 |
| | | | SD | 111.60 | 101.60 | 64.67 | 16.28 |
| | | | % CV | 17.8% | 16.9% | 26.6% | 100.6% |

BLQ = Below the Limit of Quantitation <5 ng/mL
NC = Not Calculated, only 2 replicates available Table 7 shows the calculated pharmacokinetic parameters for NVX-144 and NVX-412 after oral dosing.

TABLE 7

| Group | Compound dosed | Route | Animal Number | Rsq | T½ (h) | Tmax (h) | Cmax (ng/mL) | AUCall (h * ng/mL) | AUCINF (h * ng/mL) | AUC % Extrap (%) | Bio-avail-ability |
|---|---|---|---|---|---|---|---|---|---|---|---|
| 2 | NVX-144 Free Base | PO-Sus-pension | 202903 | 0.8599 | 1.66 | 0.5 | 436.03 | 1688.67 | 1724.46 | 2.08 | 32.8% |
| | | | 202904 | 0.9103 | 1.49 | 0.5 | 428.07 | 1762.55 | 1789.00 | 1.48 | 34.0% |
| | | | 202905 | 0.9649 | 1.01 | 1.0 | 597.75 | 1958.03 | 1965.88 | 0.4 | 37.4% |
| | | | N | 3 | 3 | 3 | 3 | 3 | 3 | 3 | 3 |
| | | | Mean | 0.9117 | 1.39 | 0.67 | 487.28 | 1803.08 | 1826.45 | 1.32 | 34.7% |
| | | | SD | 0.0525 | 0.34 | 0.29 | 95.75 | 139.18 | 124.99 | 0.85 | 2.4% |
| | | | % CV | 5.8 | 24.2 | 43.3 | 19.6 | 7.7 | 6.8 | 64.5 | 6.8% |
| 3 | NVX-412 | PO-Sus-pension | 202906 | 0.8925 | 1.28 | 1.0 | 525.49 | 2388.65 | 2412.71 | 1.00 | 45.9% |
| | | | 202907 | Missing | Missing | 1.0 | 464.23 | 1642.21 | Missing | Missing | Missing |
| | | | 202908 | 0.9292 | 1.02 | 1.0 | 584.12 | 2192.52 | 2200.54 | 0.36 | 41.9% |
| | | | N | 2 | 2 | 3 | 3 | 3 | 2 | 2 | 2 |
| | | | Mean | 0.9109 | 1.15 | 1.0 | 524.61 | 2074.46 | 2306.62 | 0.68 | 43.9% |
| | | | SD | NC | NC | 0 | 59.95 | 386.97 | NC | 0.45 | NC |
| | | | % CV | NC | NC | 0 | 11.4 | 18.7 | NC | 65.7 | NC |
| 4 | NVX-144 Free base | PO-Solu-tion | 202909 | 0.9922 | 2.39 | 0.5 | 690.75 | 2503.42 | 2763.33 | 9.41 | 52.6% |
| | | | 202910 | 0.9741 | 1.01 | 1.0 | 626.73 | 1985.89 | 1994.04 | 0.41 | 37.9% |
| | | | 202911 | 0.978 | 1.27 | 0.5 | 824.32 | 2496.24 | 2521.47 | 1.00 | 48.0% |
| | | | N | 3 | 3 | 3 | 3 | 3 | 3 | 3 | 3 |
| | | | Mean | 0.9814 | 1.56 | 0.67 | 713.93 | 2328.51 | 2426.28 | 3.61 | 46.1% |
| | | | SD | 0.0095 | 0.73 | 0.29 | 100.82 | 296.75 | 393.38 | 5.03 | 7.5% |
| | | | % CV | 1 | 47 | 43.3 | 14.1 | 12.7 | 16.2 | 139.6 | 16.2% |
| 5 | NVX-412 | PO-Solu-tion | 202912 | 0.9422 | 1.18 | 0.5 | 731.88 | 2390.36 | 2404.95 | 0.61 | 45.7% |
| | | | 202913 | 0.9736 | 0.98 | 1.0 | 686.89 | 2132.13 | 2139.39 | 0.34 | 40.7% |
| | | | 202914 | 0.9277 | 1.96 | 0.5 | 509.37 | 2224.16 | 2322.68 | 4.24 | 44.2% |
| | | | N | 3 | 3 | 3 | 3 | 3 | 3 | 3 | 3 |
| | | | Mean | 0.9478 | 1.37 | 0.67 | 642.71 | 2248.89 | 2289 | 1.73 | 43.5% |
| | | | SD | 0.0235 | 0.52 | 0.29 | 117.65 | 130.88 | 135.94 | 2.18 | 2.6% |
| | | | % CV | 2.5 | 37.6 | 43.3 | 18.3 | 5.8 | 5.9 | 126.1 | 5.9% |

Figure 7A:
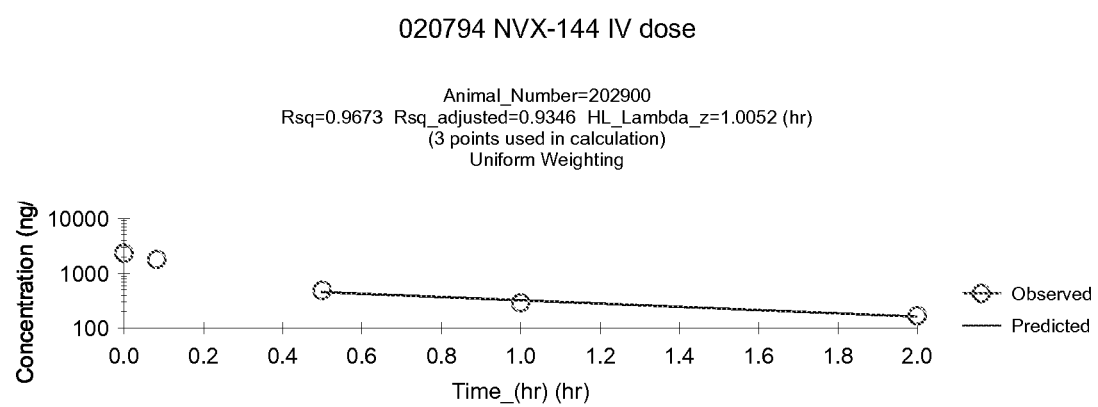
FIGS. 7A-7O show semi-log plots of pharmacokinetic data for individual animals.
Figure 7B:
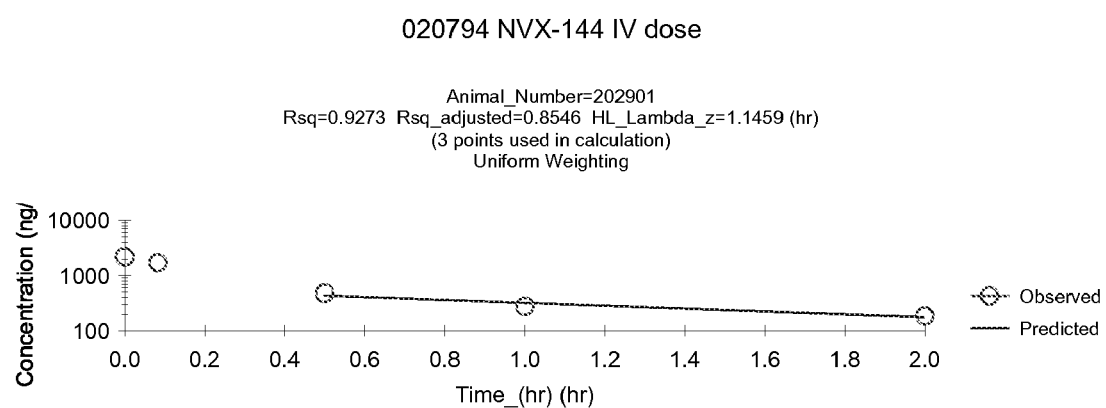
Figure 7C:
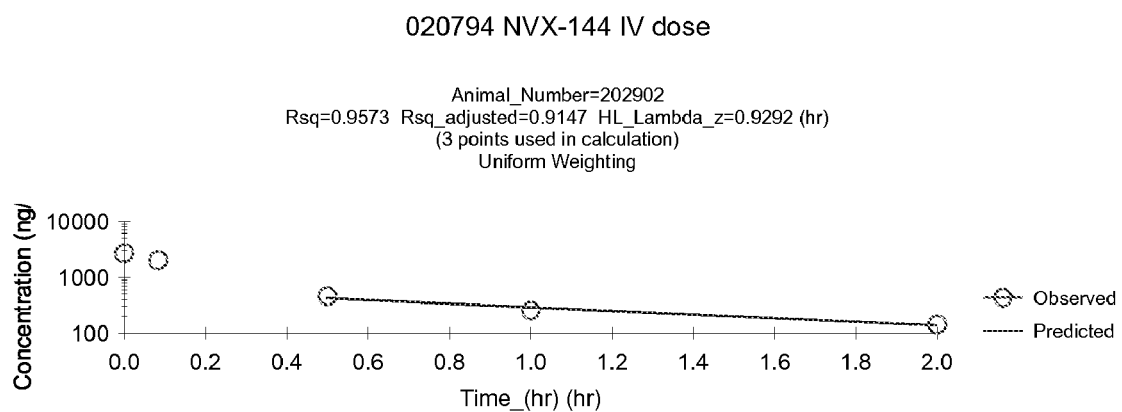
Figure 7D:
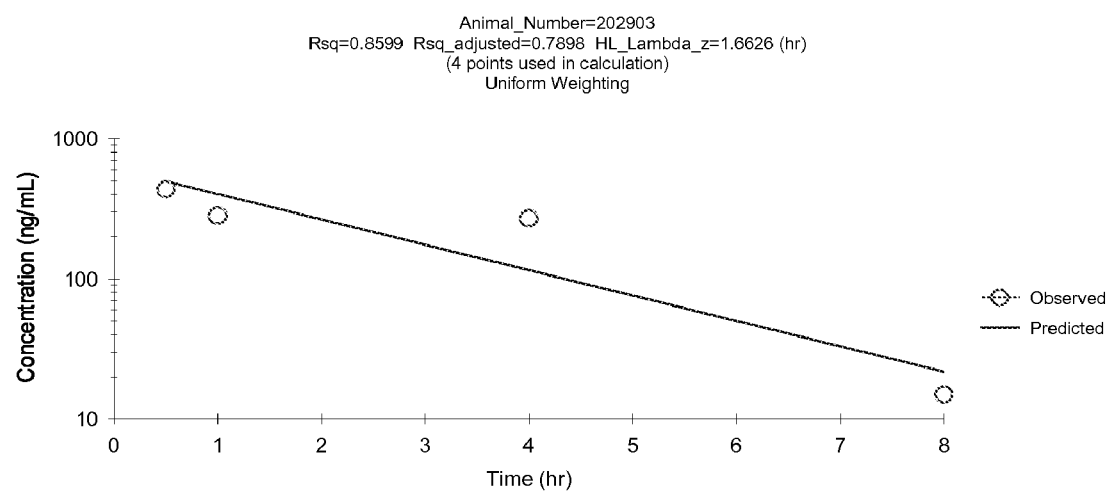
Figure 7E:
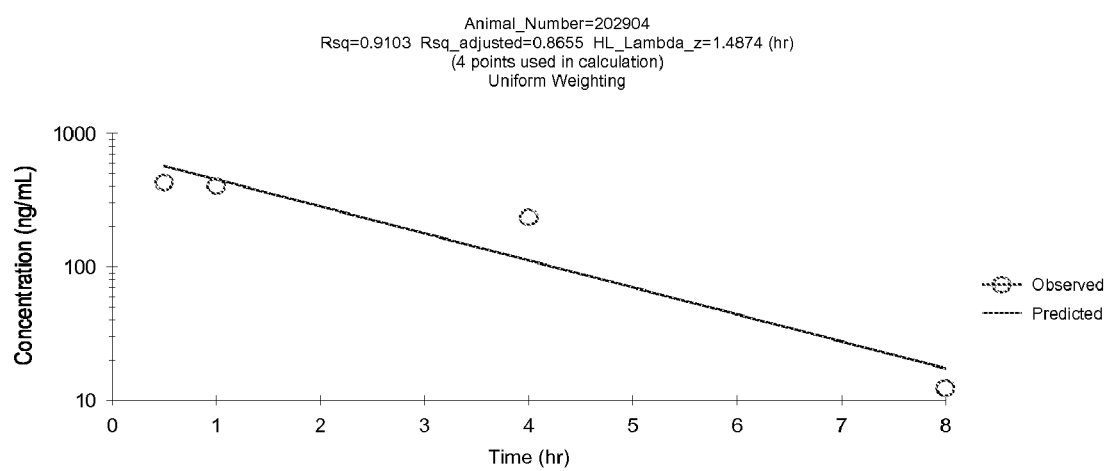
Figure 7F:
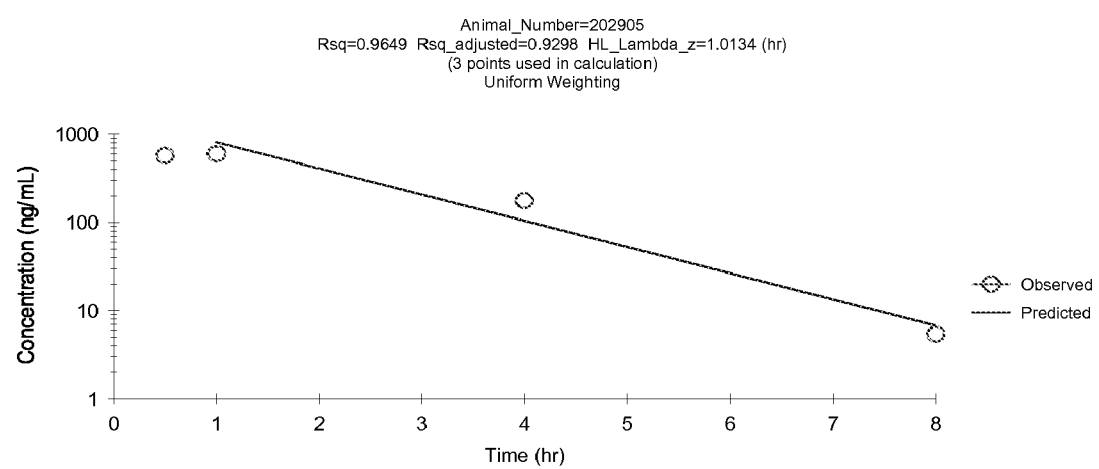
Figure 7G:
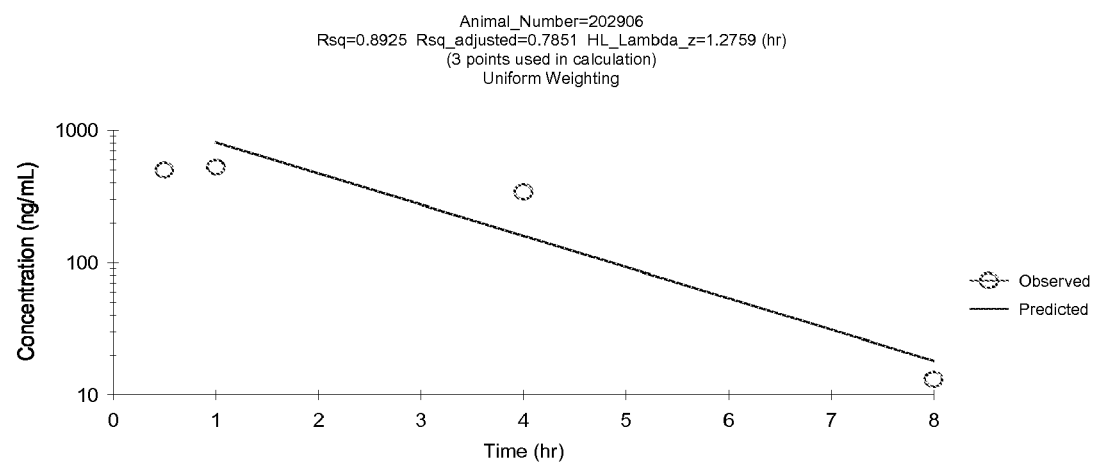
Figure 7H:
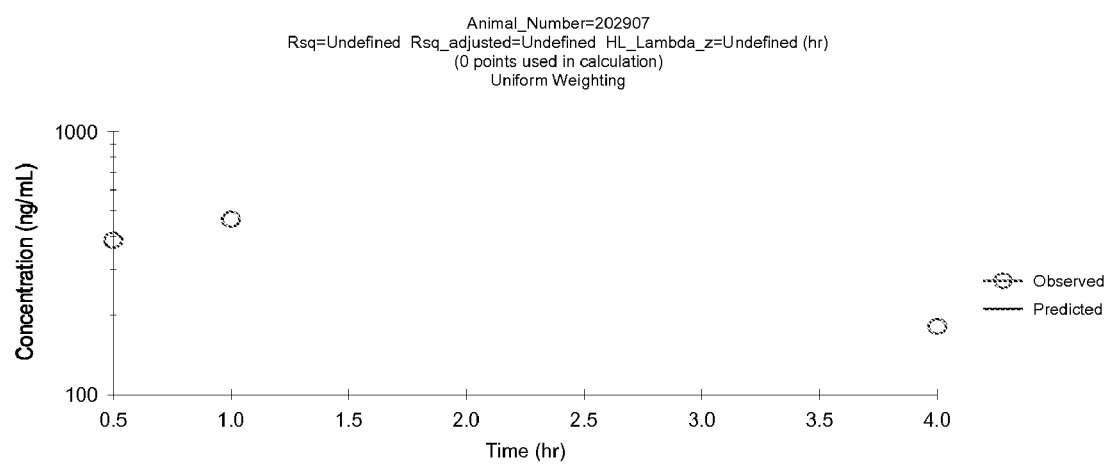
Figure 7I:
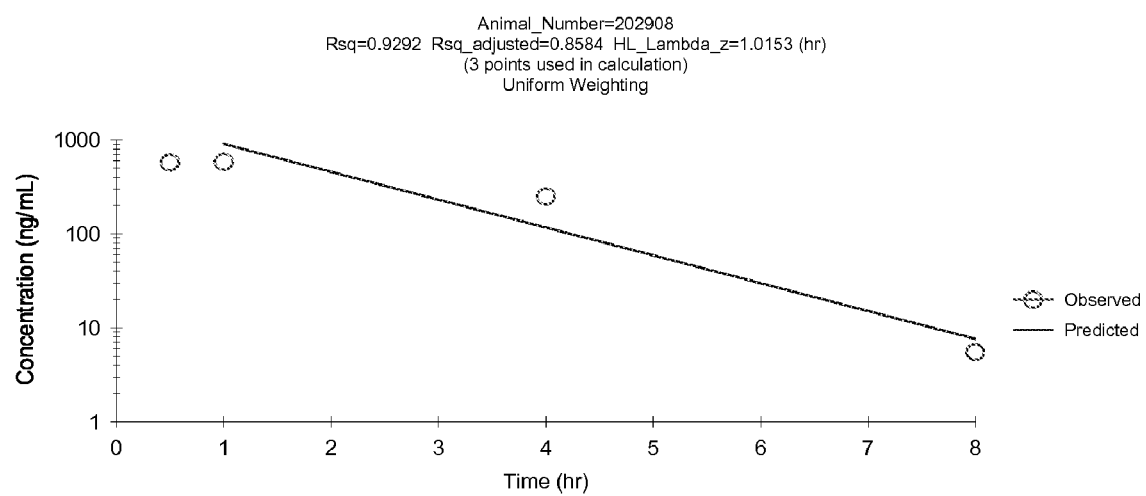
Figure 7J:
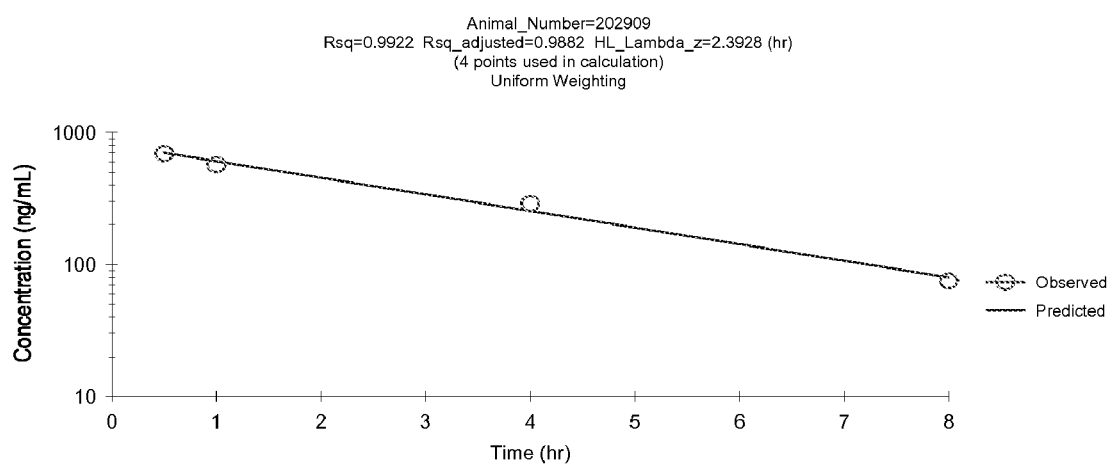
Figure 7K:
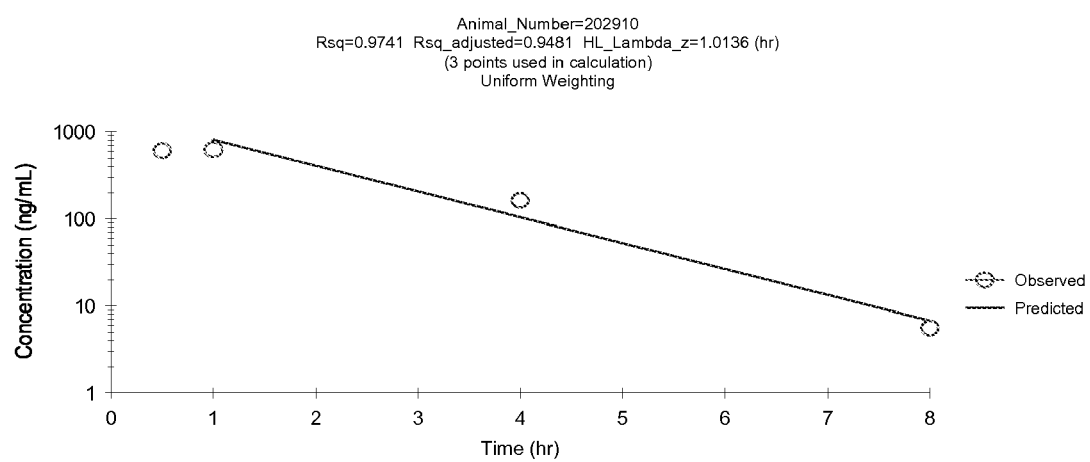
Figure 7L:
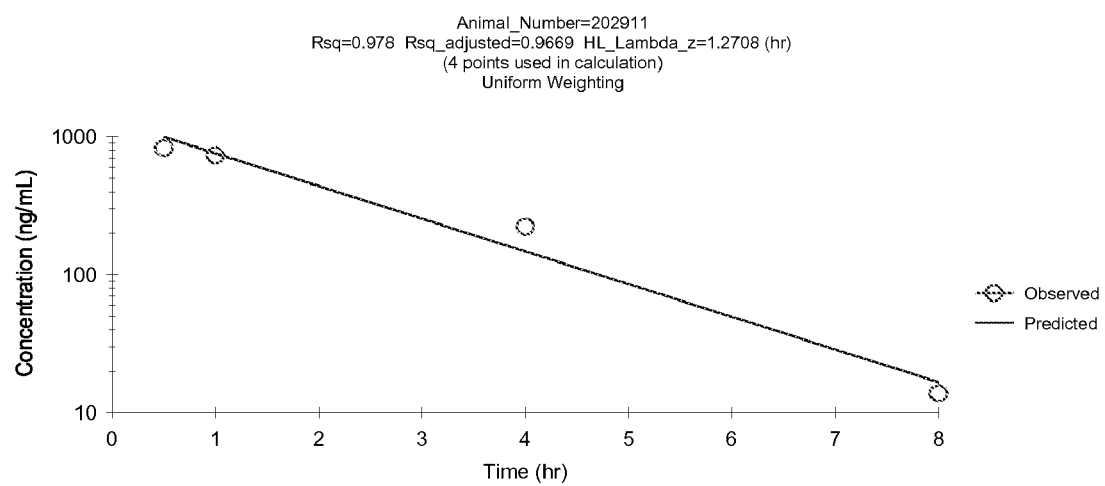
Figure 7M:
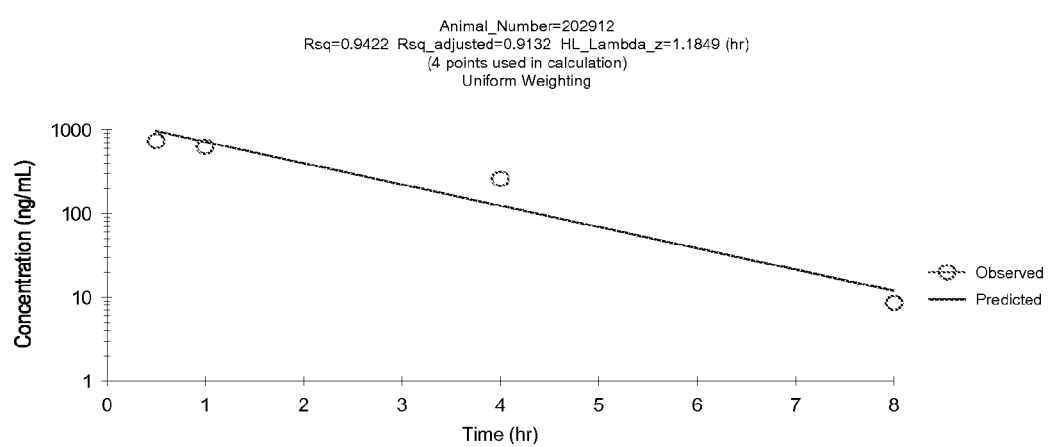
Figure 7N:
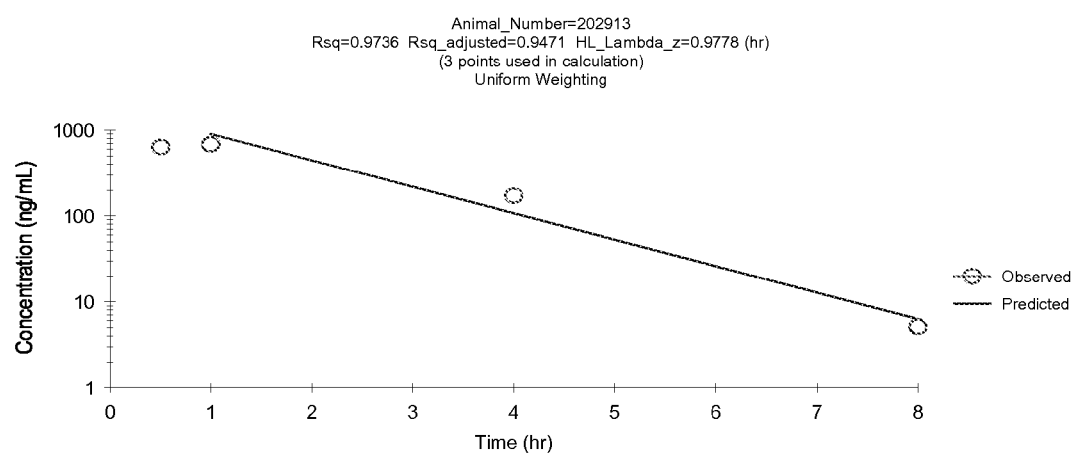
Figure 7O:
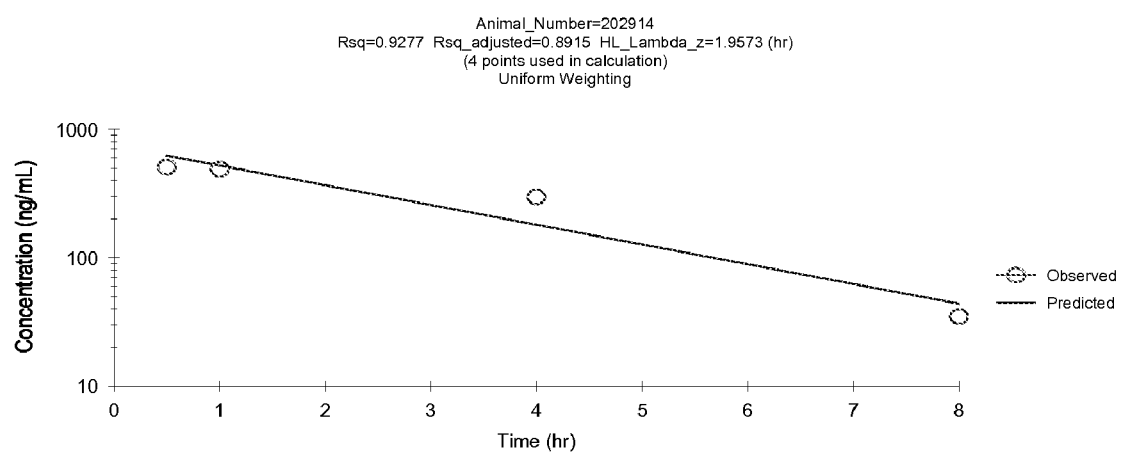
Figure 8:
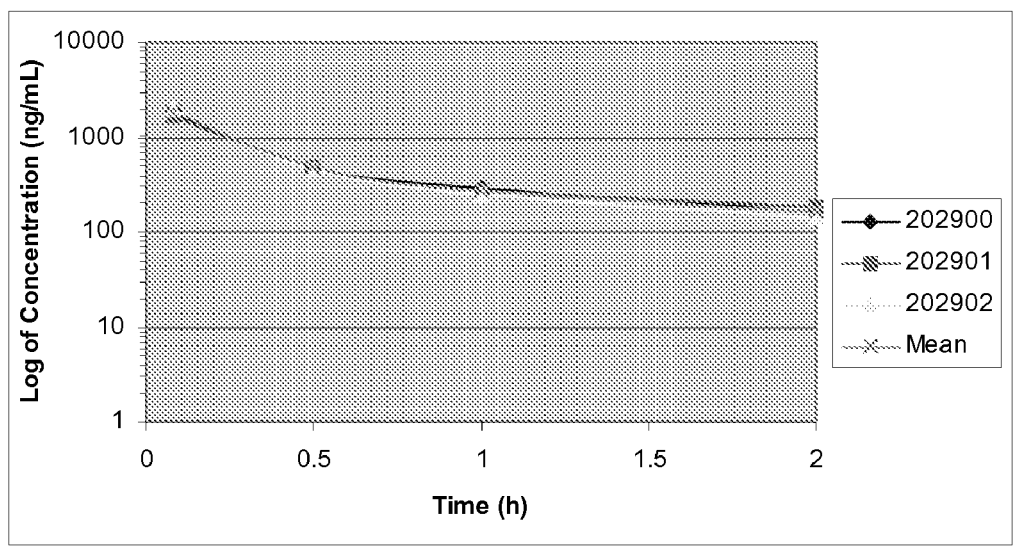
FIG. 8 shows a semi-log plot of individual and mean concentration-time data for NVX-144 dosed intravenously.
Figure 9:
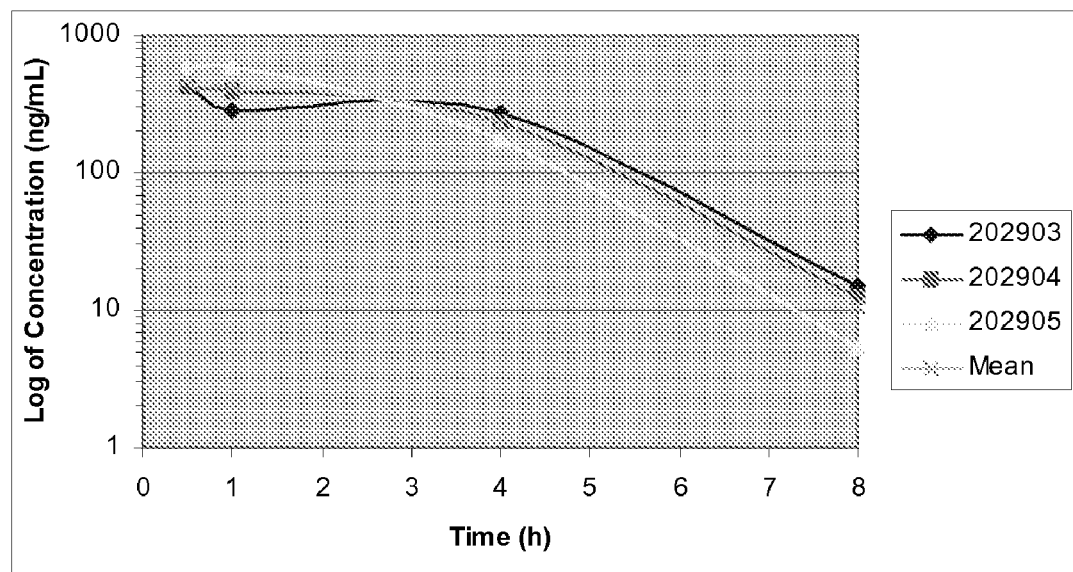
FIG. 9 shows a semi-log plot of individual and mean concentration-time data for NVX-144 free base dosed orally in suspension.
Figure 10:
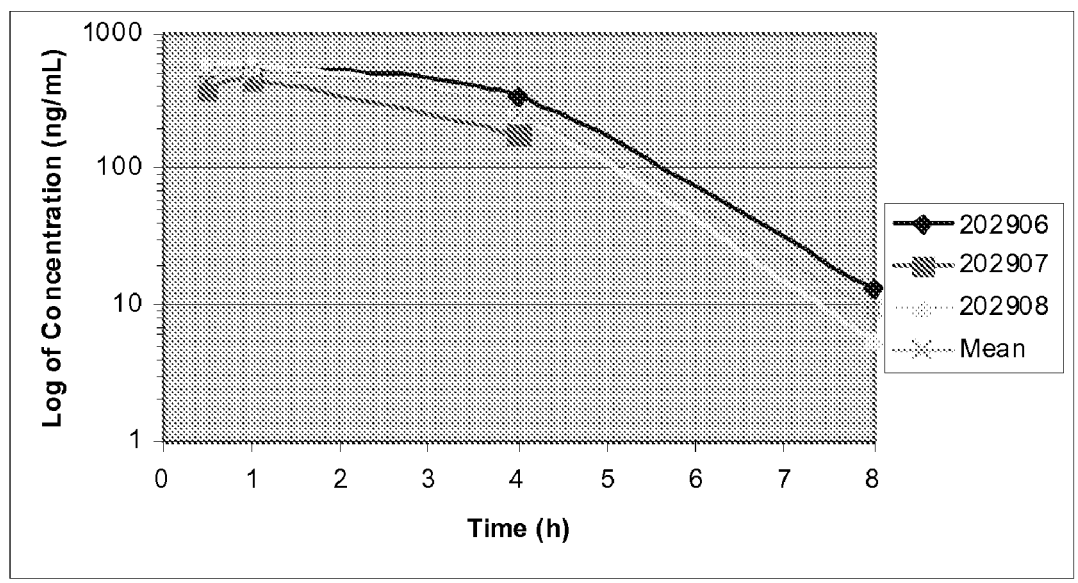
FIG. 10 shows a semi-log plot of individual and mean concentration-time data for NVX-412 dosed orally in suspension.
Figure 11:
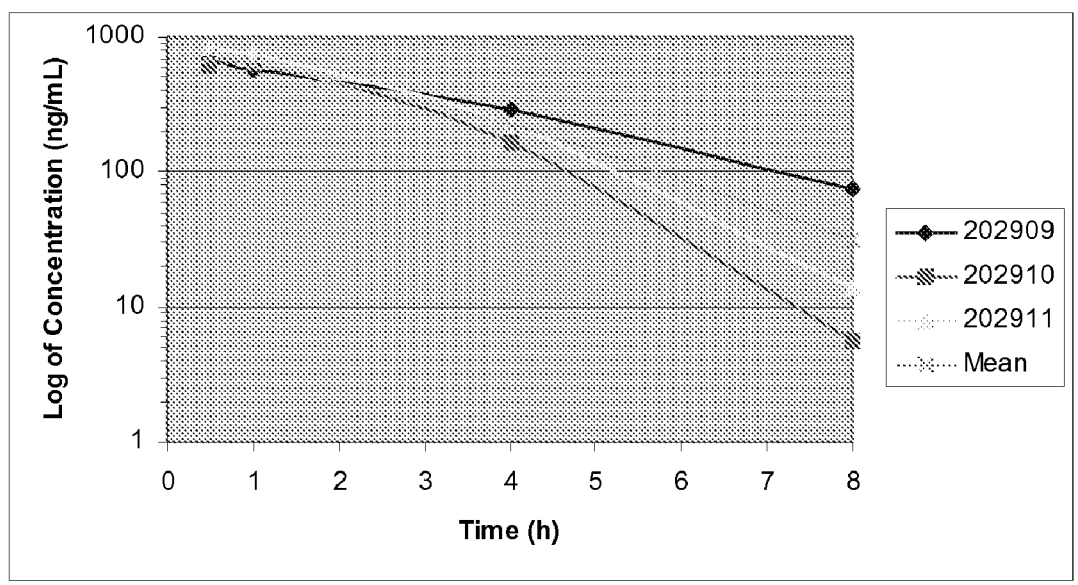
FIG. 11 shows a semi-log plot of individual and mean concentration-time data for NVX-144 free base dosed orally in solution.
Figure 12:
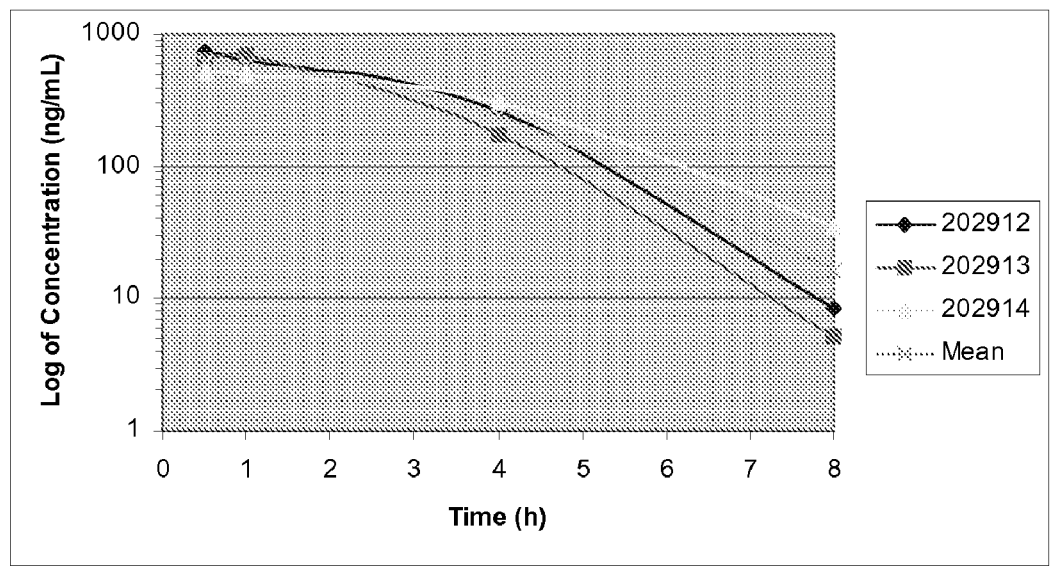
FIG. 12 shows a semi-log plot of individual and mean concentration-time data for NVX-412 dosed orally in solution.

Missing = Not Calculated; could not be calculated by WinNonLin
Bioavailability calculated using the mean AUCINF value for the IV treatment and individual AUCINF values for the PO treatment, adjusted for dose administered FIGS. 7A-7O show semi-log plots of pharmacokinetic data for each individual animal.

FIGS. 8-12 show semi-log plots of individual and mean concentration-time data for NVX-412 and for NVX-144 free base dosed intravenously, orally in suspension, and orally in solution.

Thus, it was discovered that

NVX-412 when administered IV to rats had a terminal plasma half-life of 0.93 to 1.15 hours.

NVX-412 when administered IV to rats resulted in a moderate clearance of 3806 mL/hr/kg and a moderate volume of distribution of 3985 mL/kg.

The oral absorption of NVX-144 free base when administered as a solution or suspension was moderate.

The oral absorption of NVX-412 when administered as a solution or suspension was moderate.

The oral bioavailability averaged 34.7% after oral administration of NVX-144 free base as a suspension and 46.1% after oral administration as a solution.

The oral bioavailability averaged 43.9% after oral administration of NVX-412 as a suspension and 43.5% after oral administration as a solution.

There was no significant difference in oral absorption between NVX-412 and NVX-144 free base when dosed as a solution.

There was a slight improvement in oral absorption with NVX-412 over NVX-144 free base when dosed as a suspension.

Thus, a novel co-crystal of N'-(7-fluoropyrrolo[1,2a]quinoxalin-4-yl)pyrazine-2-carbohydrazide with oxalic acid has been discovered, NVX-412. This novel compound has demonstrated good bioavailability and the ability to inhibit cancer cell growth.

While specific embodiments of the invention have been described above, such embodiments should be considered illustrative of the invention only and not as limiting the invention as construed in accordance with the claims below.

What is claimed is:

1. A co-crystal of N'-(7-fluoropyrrolo[1,2a]quinoxalin-4-yl)pyrazine-2-carbohydrazide and oxalic acid.

2. A method of preparing the co-crystal of claim 1 comprising: adding an aqueous solution of oxalic acid to an aqueous solution of N'-(7-fluoropyrrolo[1,2a]quinoxalin-4-yl)pyrazine-2-carbohydrazide.

3. A method of treating breast cancer in a human or an animal comprising, identifying a human or animal in need thereof, and administering the co-crystal of claim 1 to said human or animal.

4. The method of claim 3, wherein the co-crystal of claim 1 is administered in a quantity sufficient to treat the breast cancer.

5. The method of claim 4, wherein the co-crystal is administered orally.

6. The method of claim 4, wherein the co-crystal is administered parenterally.

7. The method of claim 4, wherein the co-crystal is administered topically.

8. The method of claim 4, wherein the co-crystal is administered to a human.

9. The method of claim 4, wherein the co-crystal is administered to an animal.

10. A pharmaceutical preparation comprising the co-crystal of claim 1.

11. A method of treating breast cancer comprising administering the pharmaceutical preparation of claim 10.

12. A composition comprising the co-crystal of claim 1 and a pharmaceutical excipient.

* * * * *